United States Patent [19]

Shukla

[11] Patent Number: 5,773,238
[45] Date of Patent: Jun. 30, 1998

[54] DROPLET CHEMICAL REACTION CHAMBER

[76] Inventor: Ashok K. Shukla, 10423 Popkins Ct., Woodstock, Md. 21163

[21] Appl. No.: 499,667

[22] Filed: Jul. 7, 1995

[51] Int. Cl.$^6$ .............................. C12P 1/00; C12N 13/00; C12N 11/04; C12N 5/00
[52] U.S. Cl. ...................... 435/41; 204/403; 435/173.1; 435/174; 435/182; 435/283.1; 435/289.1; 435/382
[58] Field of Search .............................. 435/41, 174, 177, 435/180, 182, 173.1, 283.1, 284.1, 382; 204/403

[56] References Cited

U.S. PATENT DOCUMENTS 5,401,634   3/1995   Milbrath ....................................... 435/6

*Primary Examiner*—David M. Naff

[57] ABSTRACT

A reaction chamber is constructed of a reactant-containing aqueous solution, which may be in droplet form, coated with a fluoropolymer powder such as Polytetrafluoroethylene (PTFE), preferably having a particle size of less than 500 microns. After a reaction, the droplet is destroyed by adding a substance such as a detergent or organic solvent, and the fluoropolymer powder is removed by centrifuging and filtering. Using a micropipette, size of the droplet chamber is increased or decreased by removing or adding liquid, or liquid is transferred from one droplet chamber to another. Charcoal, metal powder or silica powder can be inserted inside or on the surface of the droplet. A droplet chamber containing a first reactant such as an enzyme-bound bead is combined with a second droplet chamber containing a second reactant to react the first and second reactants. A dialysis chamber contains a filtration membrane in contact with the droplet chamber. Placing the droplet chamber between two electrodes and producing current flow between the electrodes provides an electrochemical reaction. A temperature-sensitive reaction such as the Polymerase Chain Reaction (PCR) is performed by heating or cooling the droplet chamber. The droplet reaction chamber is advantageous for microvolumes of sample since container walls are not present on which the sample can disperse, and the chamber does not require significant energy for heating or cooling. In tissue culture, coating a solution containing tissue cells with the fluoropolymer powder reduces sticking of the cells to surfaces of a container.

17 Claims, 3 Drawing Sheets

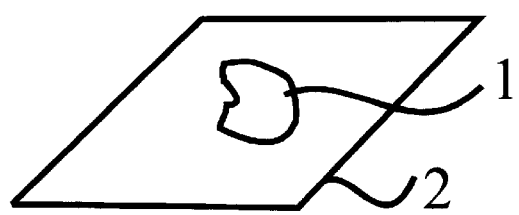
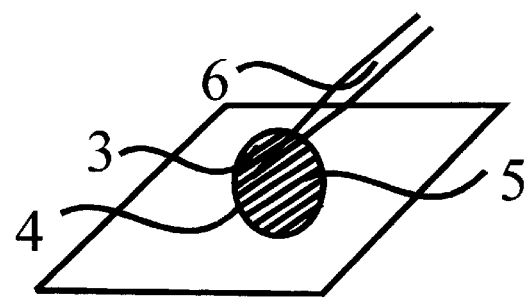
Droplet without
PTFE-Powder
Droplet with
PTFE-Powder
Fig. 1a
Fig. 1b

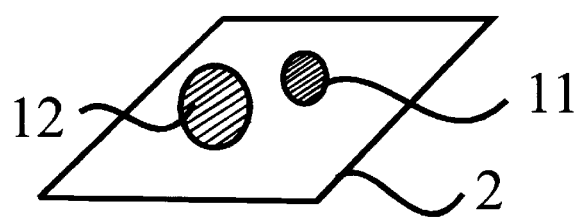
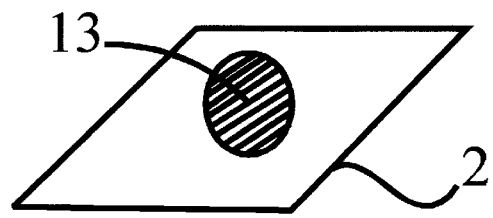
Fig. 4a                    Fig. 4b

DROPLET CHEMICAL REACTION CHAMBER

FIELD AND BACKGROUND OF THE INVENTION

1. Field of the Invention

The present invention relates in general to chambers for chemical reactions, and in particular to the construction of such chambers by application of a fluoropolymer (polymer containing fluoro group), such as Polytetrafluoroethylene (PTFE) to aqueous solutions.

The invention described and claimed herein comprises a novel chemical reaction chamber for carrying out reactions in aqueous solutions, characterized by an outer coating of a fluoropolymer, such as (PTFE).

2. Background Information

Chemical (including biochemical) reactions are frequently carried out within a chamber or other container.

In chemical and biochemical experiments, especially those involving small volumes (microvolumes) of a sample, there is always a significant loss of the sample as it disperses on the container walls.

Additionally, in reactions which are temperature sensitive, as for example the Polymerase Chain Reaction (PCR), there is also a loss of energy and time resulting from the need to heat (or cool) the reaction chamber itself.

However, when water or an aqueous solution contacts PTFE powder, it forms droplets coated with the powder. These droplets form a reaction chamber which does not involve significant loss of sample or significant energy or time loss from the heating or cooling of a reaction chamber.

If a solid insoluble material like active charcoal, metal powder, silica powder or a small piece of membrane or any other material is inserted inside or on the surface of the droplet reaction chamber, it will remain inside or on the surface.

By using a micro-pipette, liquid can be easily transferred from one droplet reaction chamber to another. The sizes of the droplets can be increased or decreased using a micropipette and eventually either by adding or removing the solution to/from the droplet reaction chamber.

These droplet reaction chambers can be used for different applications in chemical and biochemical reactions. In research laboratories, there are very often situations, when the container of the fluid can create problems while working with small volumes (in ul range). The droplet reaction chambers can be prepared in larger sizes by simply shaking the aqueous solution with the (PTFE) powder.

Objects

The foregoing problem is overcome, and other advantages are provided by a chemical reaction chamber comprising an aqueous solution coated with a fluoropolymer, such as (PTFE) powder.

Among the objects of the present invention are to provide a new and useful chemical reaction chamber which does not rely on conventional walls to contain the chemical reaction and thereby to provide a new and useful chemical reaction chamber which reduces loss of reactants and reduces the energy and time required to heat or cool the reaction.

These and other objects which will be apparent from the discussion which follows are achieved, in accordance with the invention, by providing a novel chemical reaction chamber for carrying out reactions in aqueous solutions, characterized by an outer coating of a fluoropolymer, such as (PTFE).

The various features of novelty which characterize the invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which:

FIGS. 1a and 1b are a plan view of a droplet reaction chamber, contrasting an untreated droplet (FIG. 1a) with a droplet treated to form a droplet reaction chamber (FIG. 1b).

FIGS. 4a and 4b illustrate the fusion of two droplet reaction chambers (FIG. 4a) into a single droplet reaction chamber (FIG. 4b).

DESCRIPTION OF THE PREFERRED EMBODIMENT

Figure 2:
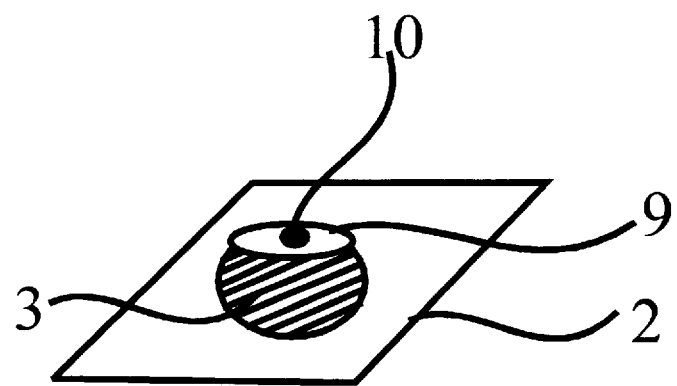
FIG. 2 illustrates a droplet reaction chamber with a membrane.

Referring to the drawings, the invention is a novel chemical reaction chamber for carrying out reactions in aqueous solutions, characterized by an outer coating of a fluoropolymer, shown in overview in FIG. 1. The operation of the invention is described with reference to a commonly available, inexpensive fluoropolymer, the perfluorocarbon (PTFE), available from DuPont under the tradename TEFLON (™). It has been found that a preferred particle size is less than 500 microns. This is by way of illustration only, and the invention could be implemented using any suitable fluoropolymer.

As shown in FIG. 1a, an aqueous solution (1) normally spreads on support surface (2). However, when an aqueous solution containing reactants of interest (3) is coated with a coating layer (4) of (PTFE), such as DuPont TEFLON (™), it forms a droplet reaction chamber (5).

The coating (4) causes the aqueous solution (3) to remain stably in a defined volume without the need for any external solid wall (except for a support [2]).

The explanation of the operation of the invention is believed to be as follows. Due to their high affinity to form hydrogen binding, the terminal fluorine atoms in a fluoropolymer, such as (PTFE), form hydrogen bonds with H-atom of water thus increasing the surface tension of the aqueous phase and enabling the formation of spherical droplets. This explanation is reinforced by the observation that the addition of alcohol or detergents to the aqueous phase destroys the droplet reaction chamber. It is believed that the addition of alcohol decreases the hydrogen-binding of H-atoms of water with fluorine atoms of (PTFE), thus lowering the surface tension of the aqueous phase and resulting in disappearance of the droplet reaction chamber. Furthermore, it has been observed that the formation of droplet reaction chambers does not take place on surfaces that contain OH—, or similar groups on the surface and thus would disturb the hydrogen-bonding of (PTFE) and water, for example, glass. Similarly, detergents lower the surface tension of aqueous phase and have a tendency to accumulate preferentially at the surface thus reducing the formation of hydrogen-bonds between fluorine atoms of (PTFE) and hydrogen atoms of water. Therefore, addition of any substance which reduces the surface tension will reduce or completely hinder the formation of droplets.

On the other hand, molecules which increase the surface tension of aqueous solution can enhance the formation of hydrogen binding between fluorine atoms of (PTFE) and OH-group of water. For example, solutes such as ionic salts increases the surface tension of aqueous solutions as compared to the surface tension of pure water. However, this increase of surface tension by addition of ionic salts is significantly smaller as compared to the decrease in surface tension by addition of detergents or alcohol. Therefore, materials which do not contain OH— or other groups that negatively influence the surface tension of aqueous solutions, will be suitable as supports for droplet reaction chambers.

(PTFE) is an ideal substance for the described uses, since it is non-toxic, chemically inert, and able to withstand extremes of heat and cold.

The reactants may be combined, then coated, or one reactant may be coated, and additional reactants introduced through the (PTFE) layer (4). One method of doing so is by insertion using a pipette (6).

Similarly, a sample of the reaction product may be withdrawn through the (PTFE) layer (4), using for example a pipette.

Figure 3:
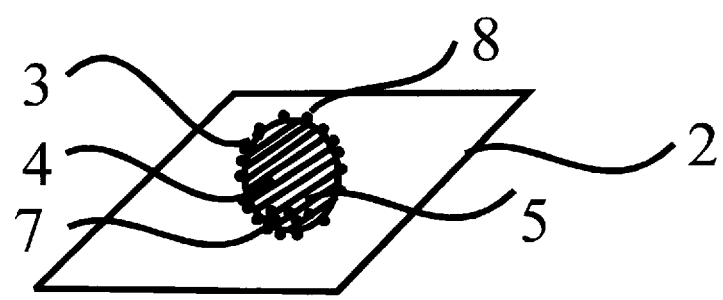
FIG. 3 illustrates a droplet reaction chamber with solid particles.

Referring to FIG. 3, in addition to reactants, the droplet reaction chamber (5) may contain solid particles, such as activated charcoal, a solid matrix for affinity purification, enzyme bound beads for biochemical reactions, cells or tissue, either within (7) the droplet reaction chamber (5) or on its surface (8).

Further processing of the droplet reaction chamber is possible. Examples include electrophoration, electroelution and electrochemical reactions, which may be accomplished by simply placing the droplet reaction chamber between electrodes. Addition of metallic powder to the droplet reaction chamber increases the current flow through the chamber.

The result of the chemical reaction may likewise be further processed, for example as follows. The droplet reaction chamber may be destroyed either by the addition of a detergent, an organic solvent or any other substance that reduces surface tension. The (PTFE) coating may then be removed from the aqueous component by centrifugation, leaving the reaction product.

Alternatively, the droplet reaction chamber may be dried and subsequently reformed by the addition of water.

Specific applications of the invention will now be illustrated.

EXAMPLE 1

Use as a chemical or biochemical reaction chamber

By pipetting an aqueous solution, buffer or reaction mixture on (PTFE) powder, a droplet reaction chamber is formed. The droplet reaction chamber can be broken in different aliquots without the loss of materials. The reactions inside the droplet reaction chamber can be started or blocked by pipetting appropriate chemicals, such as biochemicals, enzymes or inhibitors, into the droplet reaction chamber. Once the reaction is completed, the droplet reaction chamber can be centrifuged in a container containing a filter having pores smaller than the particle size of the (PTFE) powder.

EXAMPLE 2

Application in equilibrium dialysis

Referring to FIG. 2, if a membrane (9) is placed on a droplet reaction chamber (5), it floats along with the droplet reaction chamber (5). The lower surface of the membrane will be in contact with the liquid inside the droplet reaction chamber. A liquid (10) may then be placed on the upper side of the membrane for dialysis. Once equilibrium has been reached, a sample may be taken from either side of the membrane using, for example, a micropipette. Thus, the droplet reaction chamber may be used as a disposable dialyser for small samples.

EXAMPLE 3

Combining multiple reaction chambers

Referring to FIG. 4, two or more reactants may be combined as follows. Each reactant is coated with (PTFE) as described above. The resulting droplet reaction chambers may then be combined by forcing them together, resulting in rapid mixing of their contents. In FIG. 4a, two reactants are coated to form droplet reaction chambers 11 and 12, then combined to form droplet reaction chamber 13, in which a reaction between the contents of droplet reaction chambers 11 and 12 will occur, as shown in FIG. 4b.

EXAMPLE 4

Rapid temperature change

In some reactions, notably PCR, it is necessary to rapidly vary the temperature of the reactants. Using a droplet reaction chamber, the heat and time otherwise expended on changing the temperature of a solid container is not necessary.

EXAMPLE 5

Application in tissue culture experiments

Many natural cells and cell lines have a tendency to stick to the surface of containers. By gently shaking a mixture of an aqueous solution containing such cells with (PTFE) powder, the tendency to stick is reduced. Cells may be grown inside the (PTFE) coated aqueous phase in suspension. In some cases, cell growth may be improved because of the three dimensional nature of the aqueous phase. A gentle shaking of the tissue culture container can evenly distribute the cells inside the chamber.

As can be seem from the above description and examples, it is possible to carry out a wide variety of chemical and biochemical reactions using the invention, simply by providing appropriately sized droplets of an aqueous solution containing the desired reactants and by coating the droplets with (PTFE).

Thus, there has been described a novel chemical reaction chamber for carrying out reactions in aqueous solutions, characterized by an outer coating of (PTFE), that has a number of novel features, and a manner of making and using the invention.

While a specific embodiment of the invention has been shown and described in detail to illustrate the application of the principles of the invention, it will be understood that the invention may be embodied otherwise without departing from such principles and that various modifications, alternate constructions, and equivalents will occur to those skilled in the art given the benefit of this disclosure. Thus, the invention is not limited to the specific embodiment described herein, but is defined by the appended claims.

I claim:

1. A chamber for carrying out chemical reactions in aqueous solution, comprising a droplet reaction chamber, said droplet reaction chamber comprising:

an aqueous solution containing at least one reactant in droplet form; and a coating of a fluoropolymer powder on the said droplet, which maintains said aqueous solution in droplet form.

2. A chamber as in claim 1, further comprising a support for supporting said droplet reaction chamber.

3. A chamber as in claim 1 wherein said fluoropolymer powder (PTFE) is Polytetrafluoroethylene.

4. A chamber as in claim 1 wherein said fluoropolymer powder has a particle size of less than 500 microns.

5. A dialysis chamber, comprising a droplet reaction chamber as in claim 1 and further comprising a filtration membrane in contact with said droplet reaction chamber.

6. A method for carrying out a chemical reaction, comprising the steps of:

providing a first chamber as in claim 1 wherein said chamber contains a first reactant;

providing a second chamber as in claim 1 wherein said chamber contains a second reactant; and combining the chambers.

7. A method as in claim 6 wherein said first reactant comprises an enzyme-bound bead.

8. A method for tissue culture comprising the steps of:

providing an aqueous solution containing biological cells in a container; and coating said solution with a fluoropolymer powder whereby sticking of the cells is reduced to the container surface in contact with said solution.

9. A method for carrying out a temperature-sensitive chemical reaction, comprising the steps of:

providing a chamber containing a reactant as in claim 1; and heating or cooling said chamber to carry out said chemical reaction.

10. A method as in claim 9 wherein said temperature-sensitive chemical reaction is Polymerase Chain Reaction (PCR).

11. A method for chemical processing comprising the steps of:

providing a chamber as in claim 1;

reacting said reactant to carry out a chemical process within said chamber;

destroying said chamber by adding a chamber-destroying substance; and removing the fluoropolymer powder by filtration and centrifugation.

12. A method as in claim 11 wherein said chamber-destroying substance is a detergent.

13. A method as in claim 11 wherein said chamber-destroying substance is an organic solvent.

14. A method for carrying out an electrochemical process, comprising the steps of:

providing a droplet reaction chamber as in claim 1;

placing said droplet reaction chamber between two electrodes; and providing a current flow between the two electrodes to produce an electrochemical reaction.

15. A method as in claim 14 wherein said electrochemical process comprises electrophoration.

16. A method as in claim 14 wherein said electrochemical process comprises electroelution.

17. A method as in claim 14, further comprising the step of placing metal particles within or on the surface of said droplet reaction chamber.

* * * * *